(12) United States Patent
Appelt et al.

(10) Patent No.: US 10,335,518 B2
(45) Date of Patent: Jul. 2, 2019

(54) CATHETER LOCKING FORMULATION AND METHOD TO PREPARE SAME

(71) Applicants: Krzysztof Appelt, Broomfield, CO (US); Michael Lanzilotti, Broomfield, CO (US)

(72) Inventors: Krzysztof Appelt, Broomfield, CO (US); Michael Lanzilotti, Broomfield, CO (US)

(*) Notice: Subject to any disclaimer, the term of this patent is extended or adjusted under 35 U.S.C. 154(b) by 0 days.

(21) Appl. No.: 15/025,177

(22) PCT Filed: Sep. 26, 2014

(86) PCT No.: PCT/US2014/057877
§ 371 (c)(1),
(2) Date: Mar. 25, 2016

(87) PCT Pub. No.: WO2015/048559
PCT Pub. Date: Apr. 2, 2015

(65) Prior Publication Data
US 2016/0243287 A1    Aug. 25, 2016

Related U.S. Application Data

(60) Provisional application No. 61/883,182, filed on Sep. 26, 2013.

(51) Int. Cl.
*A61L 29/16* (2006.01)
*B01J 19/24* (2006.01)

(52) U.S. Cl.
CPC .......... *A61L 29/16* (2013.01); *B01J 19/2415* (2013.01); *A61L 2300/404* (2013.01); *A61L 2300/406* (2013.01); *B01J 2219/00051* (2013.01); *B01J 2219/00186* (2013.01)

(58) Field of Classification Search
CPC ........................................................ A61L 29/16
USPC ........................................................ 514/275
See application file for complete search history.

(56) References Cited

U.S. PATENT DOCUMENTS

| | | | |
|---|---|---|---|
| 4,362,699 A | 12/1982 | Verlander et al. | |
| 5,707,996 A * | 1/1998 | Parrinello | A61K 9/0019 514/256 |
| 2005/0013836 A1 | 1/2005 | Raad | |
| 2007/0093894 A1 | 4/2007 | Darouiche | |
| 2010/0318040 A1 | 12/2010 | Kelley, III et al. | |

FOREIGN PATENT DOCUMENTS

CN    101606945 A    12/2009

OTHER PUBLICATIONS

Li et al (J Chem Eng Data, 2008; 53:286-287).*

(Continued)

*Primary Examiner* — Marcos L Sznaidman
*Assistant Examiner* — Rayna Rodriguez
(74) *Attorney, Agent, or Firm* — Dale F. Regelman; Grossman, Tucker, Perreault & Pfleger, PLLC

(57) ABSTRACT

A method to prepare a catheter locking formulation, comprising in a first step, dissolving trimethoprim in propylene glycol at a temperature greater than room temperature, and in a final step, adding absolute ethanol at about room temperature to a solution of trimethoprim, propylene glycol, EDTA Calcium Disodium Hydrate, phosphate buffered saline, and glycerin.

7 Claims, 5 Drawing Sheets

(56) References Cited

OTHER PUBLICATIONS

Cold Spring Harbor Protocols (Phosphate buffered saline, 2006).*
Steczko et al., Microbial inactivation properties of a new antimicrobial/antithrombotic catheter lock solution (citrate/methylene blue/parabens), Nephrol Dial Transplant, Jan. 2009 (see abstract).
PCT/2014/057877—International Search Report and Written Opinion dated Jan. 28, 2015.
Extended European Search Report issued in related European patent application No. 14848867.9, dated May 22, 2017, 7 pages.
Gannoum, M. A., et al., "Antimicrobial Activity of B-Lock Against Bacterial and *Candida* spp. Causing Catheter-Related Bloodstream Infections," Antimicrobial Agents and Chemotherapy, Sep. 2011, p. 4430-4431.

* cited by examiner

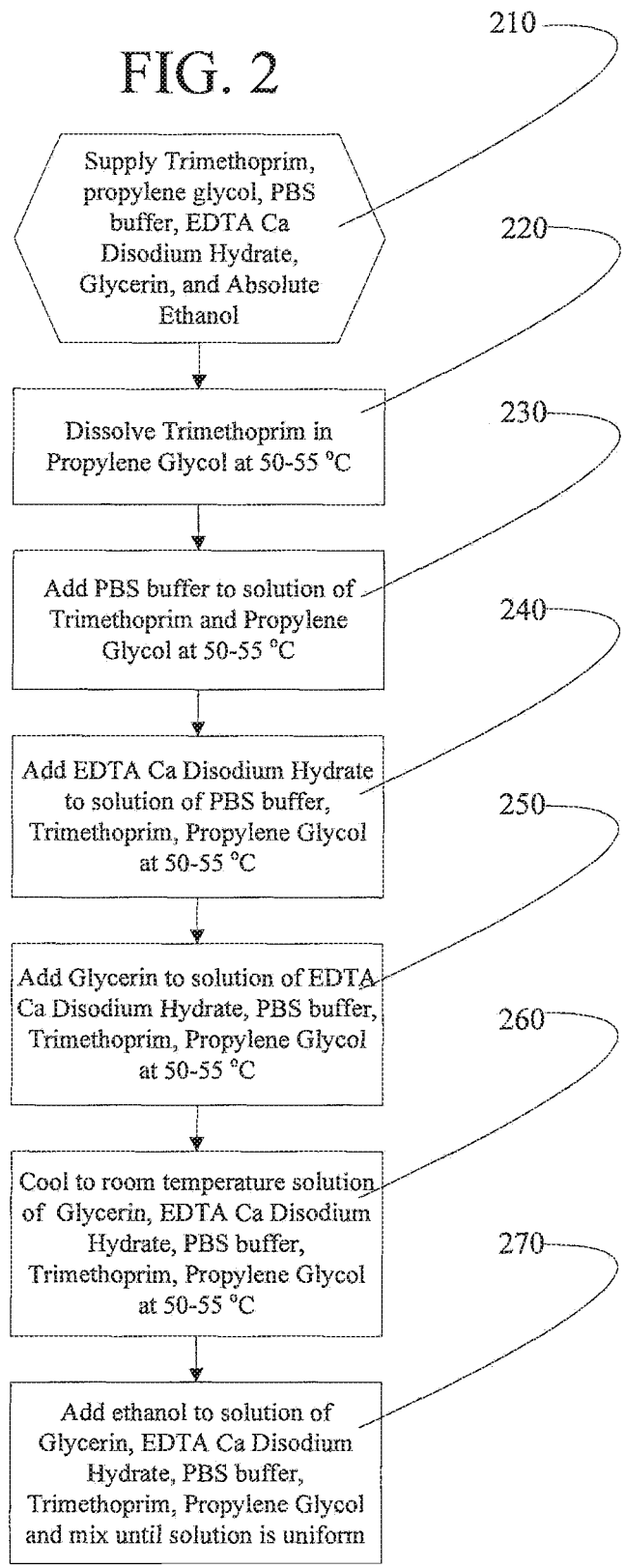

CATHETER LOCKING FORMULATION AND METHOD TO PREPARE SAME

FIELD OF THE INVENTION

The invention is directed to a catheter locking formulation and method to prepare same.

BACKGROUND OF THE INVENTION

Central venous access is an important tool for the appropriate treatment and support of patients for many life-threatening diseases such as cancer and end-stage kidney failure. However, intravascular (IV) catheters put patients at risk for catheter occlusion as well as systemic infections. Despite routine flushing with heparin or saline, 41% of central venous catheters (CVCs) result in catheter occlusion, which markedly increases the risk of infection. These infections represent a significant problem among large sections of population, are responsible for high attributable mortality (12-25%) and morbidity, and are expensive to manage (estimated cost to the healthcare system is approximately $4.6 billion per year).

Therefore, there is a need for a product that can address both catheter occlusion and infections associated with indwelling medical devices (IMDs). All CVCs when not used for their intended function such as delivery of chemo- or bio-therapeutics, parenteral nutrition, or hemodialysis must be "locked" with a Catheter Lock Solution (CLS). The locking time depends on the primary use of the catheters and it can be as short as 1 hr at Intensive Care Units (ICUs) and to up to 10 days for outpatient oncology patients.

The primary function of CLS is to provide a physical barrier to the back flow of blood into the catheter thereby maintaining catheter patency. Prior art CLS formulations contain substances such as heparin or trisodium citrate intended to prevent blood clotting within the catheter. Prior art CLS formulations also contain other substances such as taurolidine, ethanol, gentamicin or other antibiotics to inhibit microbial growth in catheter lumens.

Both Gram positive and negative bacteria including drug-resistant pathogens, as well as clinical species of fungi, commonly colonize catheter lumens and form a drug resistant microbial biofilm. Microbial biofilms can shed microbial colonies into the bloodstream leading to infections and sepsis. Therefore, prevention of biofilm formation and eradication of existing biofilm is a necessary prerequisite of successful new CLS formulations.

In the past two decades the efficacy of various innovative CLS were tested in vitro and in vivo for prevention of catheter occlusion and Central Line Associated Blood Stream Infections (CLABSI). Unfortunately most, if not all, failed the expectations. For example, a lock solution containing 4% trisodium citrate and taurolidine, while it somewhat reduced CLABSI in a clinical study, significantly increased occlusion events by causing blood coagulation inside the catheter. Similar results were reported for another citrate-containing lock solution ZURAGEN.

Another problem with citrate and taurolidine-containing lock solutions such as TAUROLOCK is the low physical stability of nearly saturated solutions and tendency to form precipitation even at small temperature changes, as noted in a TAUROLOCK CE Mark package insert. Another example of failed attempt was to use 70% ethanol as CLS in a control clinical study in oncology patients. Seventy percent (70%) ethanol has demonstrated antimicrobial activity and anticoagulation activity, nevertheless, it failed in a study due to a very low density and viscosity of 70% ethanol and the resulting difficulty to install and maintain this experimental CLS within catheter lumens.

Another problem with prior art CLS formulations, including various combinations of antibiotics and heparin or citrate, is an inability to eradicate mature biofilm. While most of them have measurable MIC (minimum inhibitory concentration) against bacteria and can prevent biofilm formation, none has proven efficacy in eradicating bacterial and fungi biofilms. After CVC insertion, the lumens are covered rapidly by a thrombin layer, rich in host-derived proteins, that forms a conditioning film and promotes surface adherence of microbial colonizers. In addition, thrombin converts soluble fibrinogen into insoluble strands of fibrin, which acts as an accelerant for biofilm formation.

A CLS that is unable to eradicate such fibrin/biofilm will fail to significantly reduce both, CLABSI and occlusion events. Finally, antibiotics frequently used in prior art CLS formulations have low solubility and reduced activity against drug resistant pathogens. Therefore, in lock solutions those antibiotics are used at concentrations very close to their saturation points which limits the physical stability of final solutions, leads to precipitation, substandard concentration and may cause bacterial resistance.

BRIEF DESCRIPTION OF THE DRAWINGS

The invention will be better understood from a reading of the following detailed description taken in conjunction with the drawings in which like reference designators are used to designate like elements, and in which:

FIG. 2 summarizes Applicants' method to prepare their catheter locking formulation;

DETAILED DESCRIPTION OF PREFERRED EMBODIMENTS

Figure 1A:
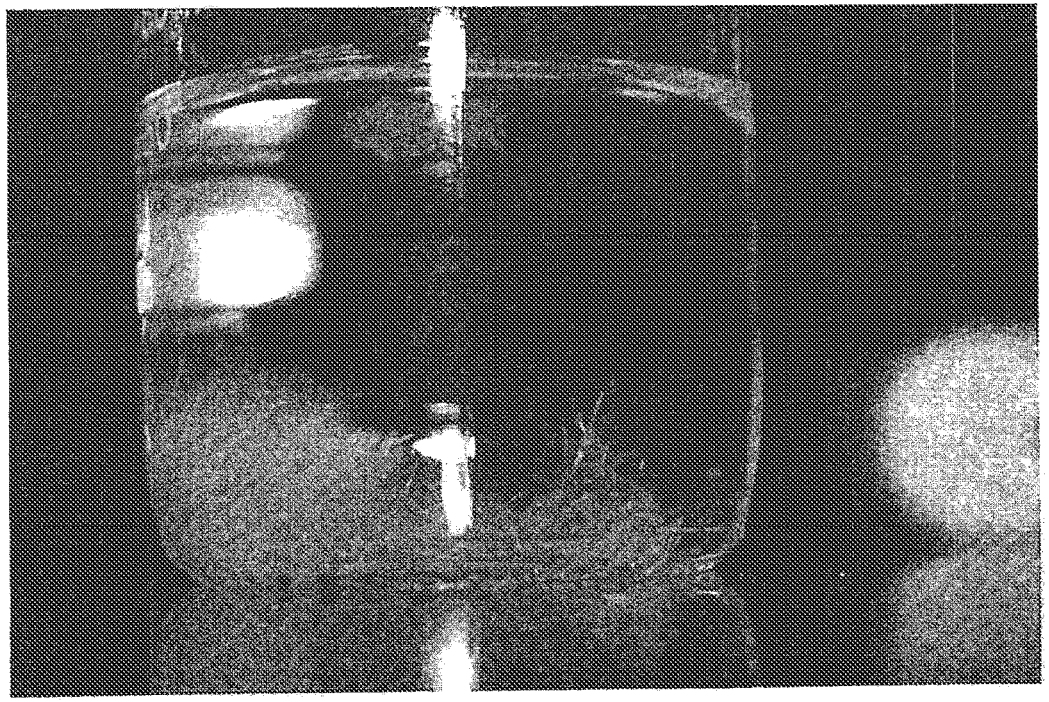
FIG. 1A shows a photograph of Sample NK-129A after 12 hours at room temperature.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart FIG. 2 included is generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Applicants have found that the many deficiencies of prior art CLS could be mitigated by development of a new and effective composition comprising the following parameters:
1. Fast acting bactericidal and fungicidal activity;
2. Synergistic antimicrobial activity of at least two components to reduce microbial resistance;
3. High, stable concentration of antimicrobial agents in final solution;
4. Eradication of mature, established biofilm inside catheter lumens;
5. Eradication/cleaning of thrombin layer, rich in host-derived proteins, which forms on lumen surface and stimulates biofilm growth and blood coagulation;
6. Prevention of blood coagulation inside catheter lumens;
7. Physiological pH between 7.5 and 8.5 to avoid blood coagulation at contact surface between CLS and blood;
8. Density similar to human blood plasma to prevent leaking of solution from lumens and pushing of solution into the lumen;
9. High viscosity for wetting the surface of catheter lumen; and
10. Stable formulation in temperature ranges from at least 0° C. to 42° C.

Early microbiological efficacy experiments tested a variety of candidate locking formulation solutions containing trimethoprim, ethylenediaminetetraacetic acid disodium (EDTA disodium) and ethanol, dissolved in dimethyl sulfoxide (DMSO), a solvent for both polar and non-polar compounds. However, DMSO is not a preferred solvent for use in human injectable products. Consequently, there was a need to develop a pharmaceutical grade catheter locking formulation using Generally Recognized As Safe (GRAS) and USP/EP Pharmacopeia ingredients acceptable for use in human injectable parenteral products, i.e. an FDAIEP approvable product.

Applicants conceptualized, designed and reduced to practice a first pharmaceutical catheter locking solution, using cGMP pharmaceutical industry requirements. Idealized product design features targeted a room temperature, sterile, clear, colorless, stable, precipitate-free formulation effective against infection-causing common and drug resistant bacteria and fungi in both planktonic and biofilm form. Key formulation design attributes included pH slightly basic to greater than 7.4, solution density, and viscosity, suitable to minimize leakage and maximize retention of the solution when locked inside indwelling catheters. Also, the solution demonstrated anticoagulative properties in the presence of blood. The desired anticoagulative properties were achieved by incorporating a chelating agent EDTA di sodium into the formulation.

A first pharmaceutical catheter locking formulation comprised USP grade ingredients of trimethoprim (1%), EDTA disodium (3%), ethanol (25% by volume), propylene glycol, glycerin and phosphate buffered saline (pH 7.4). Numerous examples of laboratory scale batches (100 ml to 500 ml) were prepared and tested for microbial effectiveness A second pharmaceutical catheter locking formulation was subsequently required, due to an untimely and unexpected FDA decision to eliminate EDTA disodium USP from injectable products. It was commonly understood that calcium disodium EDTA would not provide anticoagulative properties because the EDTA/calcium disodium molecule is already bound with calcium, and therefore, had no other binding sites available. As a result, it was thought that calcium disodium EDTA could not bind calcium from blood, which is required to prevent coagulation. For example, U.S. Pat. No. 7,601,731 teaches, in pertinent part: "For example, the well-known chelator ethylenediamine-N,N,N',N',-tetraacetic acid (EDTA) acts as an anticoagulant because it is capable of scavenging calcium ions from the blood." Col. 12 at Lines 5-8.

In spite of the teaching away of the prior art, Applicants' second formulation substituted EDTA calcium disodium for EDTA disodium. Surprisingly, substituting calcium disodium EDTA for EDTA disodium in the formulation did, in fact, provide a catheter locking formulation having anticoagulative properties as documented by Applicants' in-vitro blood coagulation experiments. These results were non-obvious, unexpected and surprising. Numerous examples of laboratory scale batches (250 ml-1000 ml) were prepared and tested.

Applicants' catheter locking formulation comprises trimethoprim, EDTA calcium disodium, ethanol, propylene glycol, glycerin, and phosphate buffered saline that is calcium and magnesium free with a pH of about 7.4.

Trimethoprim ("TMP"), Compound I, binds to dihydrofolate reductase and inhibits the reduction of dihydrofolic acid (DHF) to tetrahydrofolic acid (THF). THF is an essential precursor in the thymidine synthesis pathway and interference with this pathway inhibits bacterial DNA synthesis. Trimethoprim's affinity for bacterial dihydrofolate reductase is several thousand times greater than its affinity for human dihydrofolate reductase

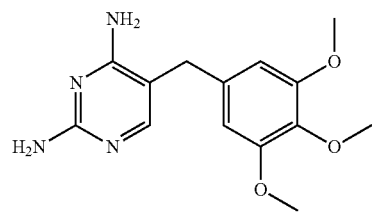

I

Table 1 recites solubility potentials for TMP, reported as (g/100 mL), as published in Analytical Profiles of Drug Substances-Trimethoprim, 1978; 7, 445-475.

TABLE 1

| | |
|---|---|
| Water | 0.04 |
| 95% Ethanol | 0.81 |

TABLE 1-continued

| | |
|---|---|
| Absolute Ethanol | 0.35 |
| Methanol | 1.21 |
| Choroform | 1.82 |
| Diethyl Ether | 0.00 |
| Carbon Tetra-Chloride | 0.002 |
| Petroleum Ether | 0.02 |
| Benzene | 0.002 |
| Acetone | 0.35 |
| Benzyl Alcohol | 7.29 |
| Dimethyl Acetamide | 13.86 |
| Propylene Glycol | 2.57 |

Table 1 indicates that TMP has essentially no solubility in water. Applicants' catheter locking formulation necessarily comprises up to about fifty (50) weight percent water. In transitioning from a DMSO-based formulation to a water-based formulation, Applicants realized that solubilization of TMP in such an aqueous formulation would be problematic. In addition, Applicants' catheter locking formulation must remain "stable" over long periods of time at room temperature or below, where by "stable" Applicants mean that the formulation does not phase separate, form an emulsion, or contain visually-perceptible solids, such as and without limitation one or more precipitates.

Initial testing and evaluation was conducted using formulations comprising TMP at about one weight percent (1 wt. %), where those formulations included up to about fifty weight percent (50 wt %) water. In order to increase the shelf stability of Applicants' catheter locking formulation, i.e. a lack of precipitates over time, the level of TMP was lowered to 0.5 weight percent for evaluation. Surprisingly, Applicants discovered that the loading of TMP could be lowered to about 0.5 weight percent (0.5 wt %) and still retain antimicrobial efficacy.

Table 2 summarizes the room temperature solubility, in various liquids, for TMP at 0.5 weight percent and EDTA Calcium Disodium hydrate at three weight percent. In short summary, TMP, at the 5 mg/mL concentration required for the said formulation is soluble only in propylene glycol, but insoluble in absolute ethanol, glycerin, and phosphate buffered saline ("PBS"). On the other hand, EDTA Calcium Disodium hydrate is soluble only in PBS, and insoluble in propylene glycol, glycerin, and absolute ethanol.

TABLE 2

Solubilities at Final Product Concentration in Formulation Solvents at 25° C.

| | Propylene Glycol | Ethanol Absolute | Glycerin | Phosphate Buffered Saline, pH 7.4 |
|---|---|---|---|---|
| Trimethoprim (Base) 5 mg/mL | Soluble | Not Soluble | Not Soluble | Not Soluble |
| EDTA Calcium Disodium Hydrate 30 mg/mL | Not Soluble | Not Soluble | Not Soluble | Soluble |

Table 3 summarizes a third embodiment of Applicants' catheter locking formulation.

TABLE 3

| Material | w/w % |
|---|---|
| Trimethoprim | 0.50 |
| EDTA Calcium Disodium Hydrate | 3.00 |
| Ethanol (Absolute 200 Proof) | 19.00 |
| Glycerin | 12.00 |
| Propylene Glycol | 19.00 |
| Phosphate Buffered Saline, USP without calcium & magnesium (PBS) | 46.50 |
| | 100.00 |

Trimethoprim is an Antimicrobial. An assay for TPM in Applicants catheter locking formulation performed using HPLC shows TMP present at a nominal level between 4.75 and 5.25 mg/mL, or about 95.0%-105.0% of a Label Claim.

Ethanol is an Antimicrobial. Table 3 reports ethanol at a nominal level of nineteen weight percent (19 wt %). Nineteen weight percent translates in a level of about 25 volume percent. A GC assay of Applicants' catheter locking formulation shows ethanol present at a nominal level between about 22.5 to about 27.5 volume percent, or about 90 volume percent to about 110 volume percent of the Label Claim.

Phosphate Buffered Saline ("PBS") utilized by Applicants comprises a pH of about 7.4, and comprises no free $Ca^{++}$ or $Mg^{++}$ ions. The PBS serves as a solvent for EDTA Ca Di sodium hydrate. In addition, Applicants' PBS has a nominal osmolality of about 287 milli-osmoles per kilogram, plus or minus 15 milli-osmoles.

Osmolality is expressed in units of solute concentration that are often used in reference to biochemistry and body fluids. Osmolality is defined in terms of osmoles. An osmole is a unit of measurement that describes the number of moles of a compound that contribute to the osmotic pressure of a chemical solution.

Applicants' catheter locking formulation comprises a high osmolality solution. In fact, the osmolality of Applicants' catheter locking solution is so high that it cannot be accurately measured. As those skilled in the art will appreciate, osmolality is often measured by freezing point depression. Applicants' catheter locking solution comprises a freezing point lowered than can be reached using commercially available osmolality-measuring equipment.

Such a low freezing point is very advantageous. Many pharmaceutical formulations exhibit freeze-thaw behavior wherein after freezing one or more components precipitates. After subsequent thawing, those one or more precipitates do not resolubilize. Applicants' catheter locking solution does not exhibit such undesirable freeze-thaw behavior.

EDTA Cu Disodium Hydrate is a Chelator. An assay of Applicants' catheter locking formulation by titration shows EDTA Ca Disodium Hydrate present at a nominal level between about 27.0 and about 33.0 mg/ml, which is between about 90 weight percent to about 110 weight percent of the Label Claim.

EDTA Ca Disodium Hydrate stabilizes the pH of Applicants' catheter locking formulation to between about 8 and about 9. TMP has a pKa of about 7.20 As those skilled in the art will appreciate, a pKa is the pH at which protonated and deprotonated fractions of a weak base, such as TMP, are about equal. Therefore, by adjusting the pH of their catheter locking formulation to between about 8 and about 9, Applicants can keep TMP in a deprotonated state, i.e. non-ionized. Keeping TMP is a deprotonated state extends the time that TMP remains in solution, resulting in increased stability for Applicants' catheter locking formulation.

Propylene Glycol is a good solvent for TMP. In addition, propylene glycol increases the viscosity of Applicants' catheter locking solution.

Glycerin increases the density of Applicants' catheter locking formulation. In addition, glycerin also increases the formulation viscosity and lubricity. Glycerin is the key ingredient to optimize formulation flow properties for syringeability. In addition, glycerin provides a bulk density required to maintain Applicants' catheter locking formulation within a catheter during the lock period.

In addition, glycerin optimizes the "wettability" of Applicants' catheter locking formulation on the interior surface of a catheter lumen. "Wetting" is the ability of a liquid to maintain contact with a solid surface, resulting from intermolecular interactions when the two are brought together. The degree of wetting (wettability) is determined by a force balance between adhesive and cohesive forces. Adhesive forces between a liquid and solid cause a liquid drop to spread across the surface. Cohesive forces within the liquid cause the drop to ball up and avoid contact with the surface.

In order for the TMP and ethanol to achieve maximal antimicrobial efficacy when Applicants' catheter locking formulation is disposed within an indwelling catheter, the locking formulation must "wet" the surface of the catheter lumen. Only if a locking formulation wets the surface of the catheter lumen can that catheter locking solution effectively prevent the formation of a microbial biofilm on the catheter lumen surface over an extended period of time. Applicants have found that glycerin is essential to provide catheter locking formulation wettability of the surface of a catheter lumen.

Applicants have further established nominal values for other parameters related to their catheter locking formulation. For example, a nominal viscosity for Applicants' catheter lock formulation is set at between about 4.0 and about 6.0 cps. (i.e. 25° C.). As those skilled in the art will appreciate, viscosity (cps) depends upon the temperature at which it is measured. At a EP compendial temperature of 0.20° C., the viscosity cps number will be higher, i.e. in the range of about 5.0 to 7.0 cps.

A nominal density for Applicants' catheter lock formulation is set at about 1.02 g/ml. A nominal pH for Applicants' catheter lock formulation is set at between about 8.0 and about 9.0. A nominal particulate matter quantification for Applicants' catheter lock formulation is set, for a container to deliver 8 mL of locking formulation, at a not more than ("NMT") level of 6000 particles having a 10 micron dimension, and a NMT level of 600 particles having a 25 micron dimension.

Applicants have set a nominal level for impurities in their catheter lock formulation. That nominal level, for individual impurities, comprises a NMT level of 0.2 weight percent. That nominal level, for total impurities, comprises a NMT level of 1.0 weight percent.

The following examples are presented to further illustrate to persons skilled in the art how to make and use the invention. These examples are not intended as a limitation, however, upon the scope of the invention.

Example 1

Process 1 for preparing Applicants' catheter locking formulation proved very difficult to develop due to conflicting ingredient dissolution behavior resulting from differing solubilities. For example, trimethoprim is soluble in propylene glycol and almost completely insoluble in water and only slightly soluble in ethanol. EDTA Ca Disodium hydrate is soluble in phosphate buffered saline and insoluble in ethanol. Applicants have discovered that, to successfully make their catheter locking formulation at the laboratory scale, specific and non-obvious formulation sequences and process steps were required. Applicants Process 1 includes the following steps.

Process 1

Step 1. Prepare Solution A—dissolve trimethoprim in propylene glycol, ethanol, glycerin at 50-55° C., where that dissolution temperature is greater than the flash point of the locking formulation.

Step 2. Prepare Solution B—dissolve EDTA calcium disodium in phosphate buffered saline (pH 7.4) at 50-55° C.

Step 3. Combine Solution B with Solution A at 50-55° C.; maintain temperature and until the mixture becomes homogeneous and stable (i.e. no precipitation). Only then reduce to room temperature.

Examples of laboratory deviations from this procedure resulted in final solution failure (i.e. ingredient precipitation) and numerous unsuccessful prototype batch preparations.

Applicants' catheter locking formulation of Table 3 comprises a solution flashpoint of between about 37° C. to about 40° C. Therefore, Process 1 requires that both Solution A and Solution B be mixed to form Applicants' catheter locking formulation at a temperature exceeding the flash point of the formulation.

A revised process was developed wherein the ethanol was added as a last step, and at room temperature. Moreover, the revised process did not require the use of multiple compounding containers which needed to be simultaneously maintained at 50-55° C.

Example 2

Two separate samples were prepared by adding trimethoprim to propylene glycol USP ("PG") in a bottle at room temperature. One bottle was placed in the 50-55° C. water bath (NK 12-129A), while the other bottle was left at room temperature (NK12-129B).

The trimethoprim of sample NK12-129A dissolved and was mostly clear within 10 minutes and completely clear within 30 minutes. The solution remained visually stable (i.e. no precipitation) when cooled to room temperature. At room temperature, phosphate buffer solution ("PBS") was added. The solution became cloudy but was visually clear after 1-2 minutes.

The trimethoprim of sample NK 12-129B remained undissolved after 30 minutes. PBS buffer was added as a possible aid to solubilization. The PBS buffer caused the trimethoprim to settle out of suspension. The sample was then heated, and the solution became clear after 55 minutes. The sample was removed from the water bath to observe for solution stability (i.e. visually clear with no precipitation}.

Figure 1B:
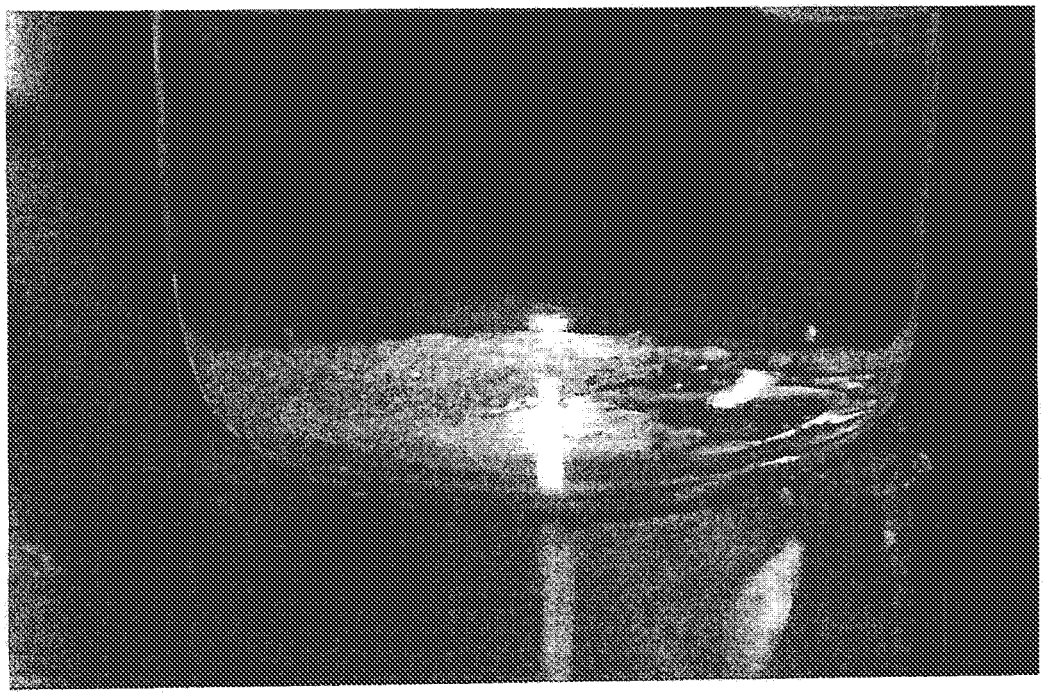
FIG. 1B shows a photograph of Sample NK-129B after 12 hours at room temperature.

After 12 hours at room temperature, both samples displayed substantial crystallization. See FIGS. 1A and 1B for photographs of the crystallized solutions. In neither sample NK-12-129A nor Nk-12-129B did the crystals resolubilize after 3 hours in the 50-55° C. water bath.

Example 3

Two samples were prepared to evaluate the order of glycerin addition. Sample NK12-130A was prepared by adding trimethoprim to PG in a bottle and heating in the 50-55° C. water bath. After the solution was completely clear, phosphate buffer solution ("PBS") buffer and glycerin were added to the bottle. A light precipitate formed initially, but the solution became clear after 30 minutes in the 50-55° C. water bath.

Sample NK 12-130B was prepared by adding trimethoprim to a PG/glycerin mixture and heating in the 50-55° C. water bath. The sample took 45 minutes to completely dissolve and become clear. When PBS buffer was added to the bottle, a light precipitate formed and was observed in the solution. The solution became clear after 30 minutes in the 50-55° C. water bath.

EDTA Ca was added to both samples, and both became clear within 10 minutes. Both samples were removed from water bath to observe for visual dissolution stability. After 12 hours at room temperature, both samples contained crystals. Sample NK 12-1308 contained more crystals than sample NK12-130A, which contained only a few crystals.

Example 4

Two samples were prepared to evaluate the order of PBS buffer addition. Sample NK12-133A was prepared by adding trimethoprim to a PG/PBS buffer mixture at room temperature. Sample NK12-133B was prepared by heating a PG/PBS buffer mixture in the 50-55° C. water bath and then adding trimethoprim. The trimethoprim did not solubilize in either sample.

Based upon the results of Examples 1-4, Applicants conclude that Trimethoprim will not solubilize in PG at room temperature. The entire pre-ethanol process is best performed at elevated temperatures in order to reduce the likelihood of non-dissolution and/or precipitation of Trimethoprim. Applicants' found that a constant dissolution temperature of 50-55° C. produces acceptable results.

Glycerin slows the solubilization of trimethoprim in PG. Glycerin also reduces solution stability if introduced too early in the process, for example, before the PBS buffer. To maintain robustness of the process, Applicants concluded that glycerin should be added only after all solids have been completely solubilized.

Furthermore, the PBS buffer inhibits the solubilization of trimethoprim in PG and can therefore only be added after the trimethoprim is completely in solution. The PBS buffer is able to solubilize EDTA Ca very easily, even after being mixed with trimethoprim and PG.

Based upon the results of Examples 2-4, Applicants defined a pre-ethanol process is as follows:
1. Measure PG into container;
2. Add trimethoprim to (1);
3. Heat batch to 50-55° C. and leave at temperature for remainder of process;
4. Allow trimethoprim to solubilize for at least one hour and/or until clear and colorless;
5. Add PBS buffer to (4). Allow to mix for at least 10 minutes;
6. Add EDTA Ca to (5). Allow to mix until all solids are dissolved;
7. Add glycerin to (6). Allow to mix until solution is uniform.

Example 5

Two samples were prepared using the pre-ethanol process described immediately hereinabove. Ethanol was added to sample NK 12-131A at room temperature and the sample was placed back in the 50-55° C. water bath for 30 minutes. The sample was then removed and allowed to cool to room temperature to observe for visual solution stability. Sample NK12-131B was removed from the water bath and allowed to cool to room temperature before ethanol was added.

Both solutions were clear and colorless and were visually stable (i.e. no precipitation) for at least 3 days.

Example 6

Two samples were prepared using the pre-ethanol process described immediately hereinabove. Both solutions were cooled to room temperature before ethanol was added. Ethanol was added to sample NK 12-133C as quickly as possible. Ethanol was added to sample NK12-1330 slowly, in dropwise fashion, over a 2-3 minute period. Both solutions were clear and colorless within 5 minutes.

Example 7

Four samples were prepared using the pre-ethanol process described immediately hereinabove. Ethanol was added in approximately the following quantities by weight:
Sample NK 12-142A-5%
Sample NK2-142B-10%
Sample NK12-142C-15%
Sample NK 12-1420-20%

Crystals formed in sample NK12-142A when left overnight at room temperature. The remaining solutions remained clear and colorless for at least 48 hours.

Example 8

Four solutions were prepared using the described pre-ethanol process. Samples NK 12-146A and NK 12-146B were quickly chilled to 25° C. using an ice bath.

Sample NK 12-146A was removed from the ice bath and ethanol was added. The solution was visually clear and stable for over 24 hours at room temperature.

Sample NK12-146B was left in the ice bath with no ethanol. High levels of crystallization were observed after 24 hours.

Samples NK12-147A and NK12-1460 were placed in a 25° C. water bath. Sample NK 12-147A was removed from the water bath and ethanol was added. The solution was visually clear and stable overnight at room temperature. Sample NK 12-1460 was left in the water bath with no ethanol. Light crystallization was observed overnight.

Based upon the results of EXAMPLES 4-8, Applicants determined that ethanol can be added to a room temperature in-process catheter locking solution as the final ingredient. In addition, solutions can be brought to room temperature quickly with no observed negative impact on the visually clear solution stability of the final lock solution.

In summary, the rate of ethanol addition to the in-process lock solution is not crucial. Ethanol is the crucial component to maintain visually clear solution stability. The minimum quantity of ethanol required to impart extended shelf stability at temperatures between 0° C. to about 42° C. in their catheter locking formulation is about 10 weight percent. This was a surprising result given that TMP is not soluble in ethanol (at the final formulation concentration.)

Based upon EXAMPLES 2-8, Applicants Process 2 for preparing a stable solution consists of the following steps.

Process 2

1. Measure PG into container;
2. Add trimethoprim to (1);

3. Heat batch to 50-55° C. and leave at temperature for remainder of process;
4. Allow trimethoprim to solubilize for at least one hour and/or until clear and colorless;
5. Add PBS buffer to (4). Allow to mix for at least 10 minutes;
6. Add EDTA Ca Disodium Hydrate to (5). Allow to mix until all solids are dissolved;
7. Add glycerin to (6). Allow to mix until solution is uniform;
8. Cool solution to room temperature; and
9. Add ethanol and mix until solution is uniform.

In certain embodiments, Applicants use a process to form their catheter locking solution wherein a previously-prepared phosphate buffer solution is not utilized. Rather, in this embodiment of Applicants' method water and various salts are added to a heated solution of trimethoprim in propylene glycol prior to the addition of glycerin, EDTA Calcium Disodium hydrate, or ethanol.

In certain embodiments, Applicants' "water and salts" Process 3 consists of the following steps:

Process 3

1. Weigh propylene glycol into a suitable process container;
2. Weigh Trimethoprim and add to the propylene glycol in the container of step 1;
3. Heat the propylene glycol/trimethoprim mixture of step 2 to 50-55° C. and maintain at this temperature for the duration of the process. Note-Trimethoprim must be completely dissolved and the solution clear and colorless (complete dissolution observed to take a minimum of one hour);
4. Weigh sterile water for irrigation and add to the 50-55° C. propylene glycol/trimethoprim solution of step 3. Mix until solution is completely clear and uniform;
5. Add NaCl, KH$_2$PO$_4$, Na$_2$HPO$_4$ to the solution of step 4;
6. Weigh EDTA Ca and add to the solution of step 5. Mix until all solids are completely dissolved;
7. Weigh glycerin and add to the solution of step 6. Mix until solution is completely clear and uniform;
8. Remove the solution of step 7 from heat and allow to cool to room temperature (25±5° C.); and
9. Weigh ethanol and add to the solution of step 8. Mix until completely clear and uniform.

Table 4 summarizes the components used in this third embodiment of Applicants' process.

TABLE 4

| Material[1] | w/w % |
|---|---|
| Trimethoprim | 0.50 |
| EDTA Calcium Disodium Hydrate | 3.00 |
| Ethanol (Absolute 200 Proof) | 19.00 |
| Glycerin | 12.00 |
| Propylene Glycol | 19.00 |
| Sterile Water for Irrigation | 46.0400 |
| Sodium Chloride (NaCl) | 0.4131 |
| Potassium Phosphate Monobasic (KH$_2$PO$_4$) | 0.0066 |
| Dibasic Sodium Phosphate (Na$_2$HPO$_4$ | 0.0365 |
| | 100.00 |

In certain embodiments, Applicants use Process 4 to form their catheter locking solution wherein a previously-prepared phosphate buffer solution is not utilized. Rather, in this embodiment of Applicants' method water without salts is added to a heated solution of trimethoprim in propylene glycol prior to the addition of glycerin, EDTA Calcium Disodium hydrate, or ethanol.

In certain embodiments, Applicants' "water without salts" method consists of the following steps:

Process 4

1. Weigh propylene glycol into a suitable process container;
2. Weigh Trimethoprim and add to the propylene glycol in the container of step 1;
3. Heat the propylene glycol/trimethoprim mixture of step 2 to 50-55° C. and maintain at this temperature for the duration of the process. Note-Trimethoprim must be completely dissolved and the solution clear and colorless (complete dissolution observed to take a minimum of one hour);
4. Weigh sterile water for irrigation and add to the 50-55° C. propylene glycol/trimethoprim solution of step 3. Mix solution until completely clear and uniform;
5. Weigh EDTA Co and add to the solution of step 4. Mix until all solids are completely dissolved;
6. Weigh glycerin and add to the solution of step 5. Mix until solution is completely clear and uniform;
7. Remove the solution of step 6 from heat and allow to cool to room temperature (25±5° C.); and
8. Weigh ethanol and add to the solution of step 7. Mix until completely clear and uniform.

Table 5 summarizes the components used in this fourth embodiment of Applicants' process.

TABLE 5

| Material | w/w % |
|---|---|
| Trimethoprim | 0.50 |
| EDTA Calcium Disodium Hydrate | 3.00 |
| Ethanol (Absolute 200 Proof) | 19.00 |
| Glycerin | 12.00 |
| Propylene Glycol | 19.00 |
| Sterile Water for Irrigation | 46.50 |
| | 100.00 |

Two different catheter locking formulations were prepared at the 100 gram laboratory scale, the first using the formulation of Table 3, and the second using the water only formulation of Table 5. To focus solely on the effects of trimethoprim solubility. both processes were stopped prior to the addition of EDTA Ca, glycerin or ethanol.

Example 9

Sample NK12-149A was prepared using steps 1-5 of Process 2. The sample became cloudy as the room temperature PBS was added, but became clear after a few minutes after equilibrating back to 50-55° C. The sample was cooled to room temperature and remained overnight. A light crystal-like precipitation was observed. The crystals did not resolubilize when the sample was re-heated to 50-55° C.

Example 10

Sample NK12-149B was prepared using steps 1-5 of Process 4. The sample became cloudy as the room temperature sterile water for irrigation was added, but became completely clear after 45 minutes. The sample was cooled to room temperature and remained overnight. A heavy crystal-like precipitation was observed. The crystals did not resolubilize when the sample was re-heated to 50-55° C. Results of this Example 10 showed adding water only to the propylene glycol/trimethoprim solution stressed trimethoprim solubility more than adding PBS in Process 2.

Several catheter locking formulations were prepared at the 100 gram laboratory scale using the formulation of Table 3 and Process 2, water only formulation of Table 5 and Process 4, and the water and salts formulation of Table 4 and Process 3, to determine how alterations in the buffer addition step affect final solution pH.

Example 11

Sample NK 12-150A was prepared as a control solution using the Formulation of Table 1 formed using Process 2. The final solution was clear. colorless and visually stable after remaining overnight at room temperature.

Example 12

Sample NK12-150B was prepared using the water only formulation of Table 5 and Process 4. The final solution was clear, colorless and visually stable after remaining overnight at room temperature.

Example 13

Sample NK12-150C was prepared using the water And salts formulation of Table 4. The buffer salts were added simultaneously with the sterile water for irrigation in rather than with the EDTA Ca. The buffer salts took 30 minutes to solubilize. The final solution was clear, colorless and visually stable after remaining overnight at room temperature.

Example 14

Sample NK12-150D was prepared using the water and salts formulation of Table 4 and Process 3. The final solution was clear, colorless and visually stable after remaining overnight at room temperature.

Room temperature pH measurement of samples 150A, 150B, 150C, and 150D, are recited in Table 6 for comparison of short-term pH stability.

TABLE 6

| Sample | Initial | 3 Days | 5 Days |
| --- | --- | --- | --- |
| NK12-150A | 8.59 | 8.71 | 8.54 |
| NK12-150B | 8.86 | 8.80 | 8.43 |
| NK12-150C | 8.63 | 9.08 | 8.76 |
| NK12-150D | 8.62 | 8.78 | 8.47 |

Two catheter locking solution examples were prepared at 1 liter scale to observe the effects of scale-up on solution preparations and to allow greater precision in measurement of raw materials, particularly buffer salts. Solutions were stirred throughout the manufacturing process using magnetic stir bars.

Example 15

Sample NK12-151B was prepared using the water only formulation of Table 5 and Process 4. The final solution was clear, colorless, and visually stable for over 48 hours at room temperature.

Example 16

Sample NK12-151C was prepared using the water and salts formulation of Table 4 and Process 3. The final solution was clear, colorless and visually stable for over 48 hours at room temperature.

Room temperature pH of each the solutions of Examples 15 and 16 are recited in Table 7 for comparison of short-term pH stability.

TABLE 7

| Sample | 2 Days | 3 Days |
| --- | --- | --- |
| NK12-151B | 8.85 | 8.91 |
| NK12-151C | 8.54 | 8.72 |

Example 17

Sample NK 12-154 was prepared at 7 liter scale using the formulation of Table 3 and Process 2. A magnetic stir bar and hot plate were used throughout the process rather than a heated water bath.

The trimethoprim took 40 minutes to dissolve after the solution reached 50-55° C. (2 hours total including ramp to temperature). The solution became clear almost immediately after adding room temperature PBS. After a few moments the solution became cloudy and remained so until the temperature returned to 50-55° C.

The EDTA Ca dissolved as quickly as it was dispersed into the solution. Glycerin was added and allowed to mix until the solution was uniform. The solution was then cooled to 25-30° C.

After the solution cooled and ethanol was added, the solution separated into three distinct layered phases. The lower layer was completely clear and comprised approximately 80% of the volume of the mixture. The middle layer was approximately 3 cm thick and also appeared clear. The upper layer was approximately 0.5 cm thick and appeared white and slightly opaque. The layer did not contain any visible undissolved solids.

The magnetic stirring was increased to more quickly disperse the three layers, resulting in a layered vortex. As mixing continued. the upper two layers became thinner as they were slowly incorporated into the lower layer. After mixing overnight at room temperature, the solution appeared clear and colorless.

Example 18

Sample NK 12-156 was prepared at 10 liter scale using the water and salts formulation of Table 4 and Process 3. A magnetic stir bar and hot plate were used throughout the process rather than a heated water bath. The propylene glycol was heated to 55° C. before addition of trimethoprim.

Trimethoprim was added as quickly as possible, to more closely simulate a larger scale manufacturing environment. Large solid clumps formed, but the material was completely dissolved within 25 minutes.

Sterile water for irrigation was preheated to 45° C. before it was added to the solution. The solution became clear almost immediately and remained clear. The total solution temperature remained above 50° C. throughout the water addition.

The buffer salts were added and completely solubilized within 20 minutes. The EDTA Ca was added and dissolved as quickly as it dispersed. Glycerin was added and allowed to mix until the solution was uniform. The solution was then cooled to 25-30° C.

The solution precipitated very light particles while cooling. The particles disappeared as mixing continued. After the solution cooled and ethanol was added, the solution separated into three distinct phases (as with Sample NK12-154). The upper white layer contained large white solid particles, approximately 1 cm×0.5 cm. After mixing overnight, the solution appeared completely clear, colorless and visually stable for at least 48 hours.

Example 19

Sample NK12-157 was prepared at 10 liter scale using the water and salts formulation of Table 4 and Process 3, a magnetic stir bar and hot plate were used throughout the process rather than a heated water bath.

Propylene glycol was heated to 70-75° C. before addition of trimethoprim. The trimethoprim was completely solubilized within 2 minutes. A light cloud formed in the headspace of the closed container. The vapor dissipated after an additional 2 minutes.

Sterile water for irrigation was preheated to 55° C. before it was added to the solution. The solution became clear almost immediately and remained clear. The buffer salts were added and completely solubilized within 10 minutes.

The EDTA Ca was added and dissolved as quickly as it was dispersed into the solution. Due to timing constraints, the solution was only cooled to 35° C. before ethanol was added. The solution separated into two distinct clear phases. No white upper layer was formed. After mixing overnight, the solution appeared completely clear, colorless and visually stable for at least 48 hours.

Table 7 recites a room temperature pH for each of the larger scale preparations of Examples 17, 18, and 19.

TABLE 8

| Sample | Initial | 2 Weeks |
|---|---|---|
| NK12-154 | 8.59 | 8.62 |
| NK12-156 | 8.73 | 8.40 |
| NK12-157 | 8.45 | 8.48 |

Solutions prepared with sterile water for irrigation only showed less robust pH stability than those prepared with buffer salts.

Example 20

Figure 3:
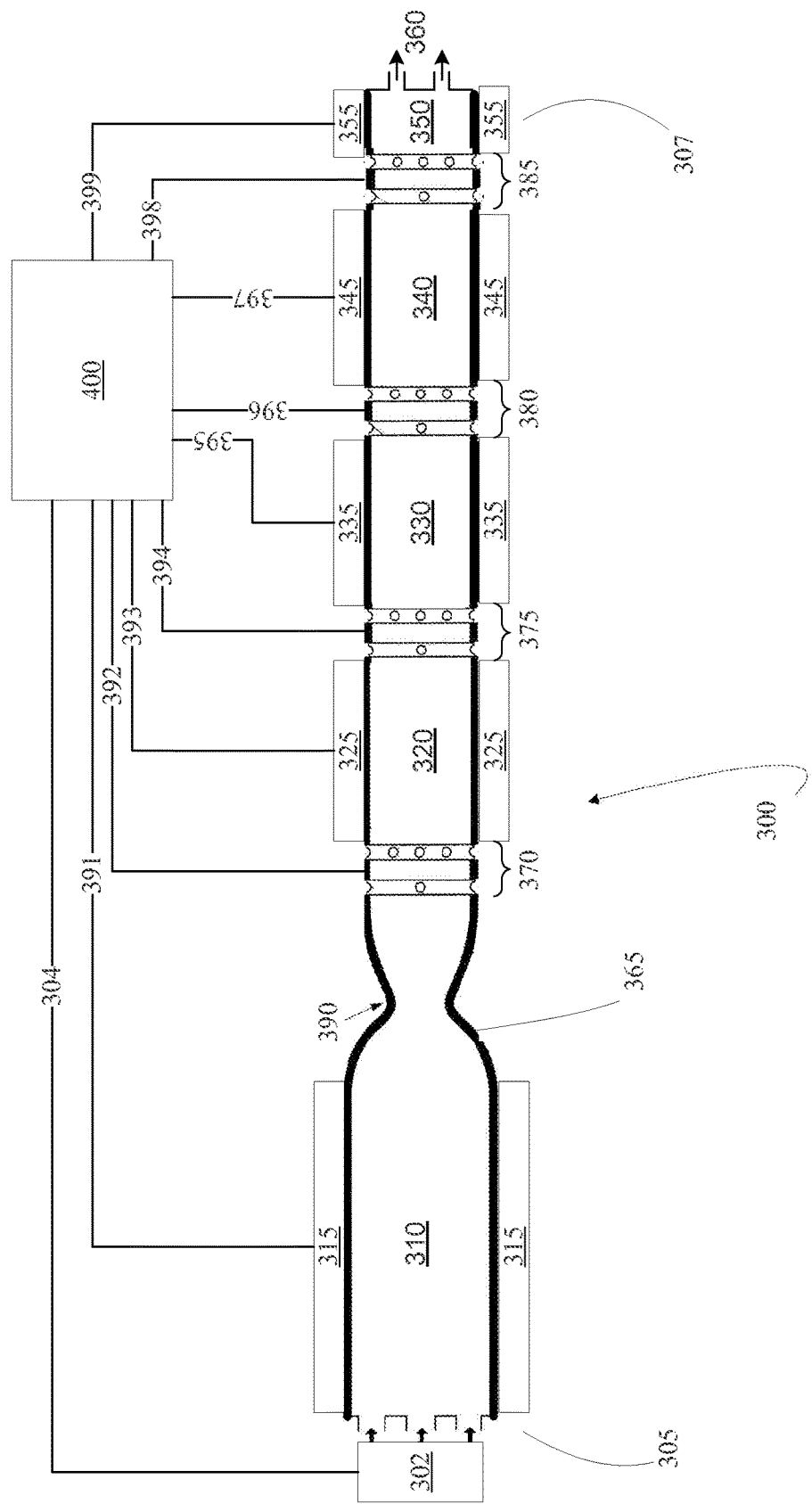
FIG. 3 illustrates one embodiment of Applicants' continuous flow reactor used to prepare their catheter locking formulation.

In certain embodiments Applicants' catheter locking formulation is made in a continuous flow reactor, such as continuous flow reactor 300 (FIG. 3). Referring now to FIG. 3, continuous flow reactor 300 comprises reactor wall 365. In certain embodiments, wall 365 is formed from stainless steel or other pharmaceutically acceptable materials. In certain embodiments, wall 365 is formed from a material that is transmissive with respect to infrared energy. In certain embodiments, wall 365 is formed from a material that is transmissive to microwave energy.

In the illustrated embodiment of FIG. 3, reactor wall 365 is formed to include a turbulent flow zone, where that turbulent flow zone is defined by a narrowing in the diameter of the reactor followed by an expansion in the diameter of the reactor at portion 365 of continuous reactor 300. The narrowing/expansion at portion 365 generates maximal turbulent flow within reactor 300 in that portion thereby facilitating mixing and dissolution. FIG. 3 illustrates a single narrowing/expansion portion 365. FIG. 3 should not be taken as limiting. In certain embodiments, continuous flow reactor 300 comprises a plurality of narrowing/expansion portions 365.

Reactor 300 comprises one or more first nozzles in fluid communication with an input pump assembly 302 disposed adjacent input end 305. Input pump assembly is in communication with controller 400 via communication link 304.

Reactor 300 comprises a first dissolution zone 310 immediately downstream from the input end 305, and a first annular heating assembly 315 disposed around first dissolution zone 310. First annular heating assembly 315 is in communication with controller 400 via communication link 391.

In certain embodiments, first annular heating assembly 315 comprises an electric heater. In certain embodiments, first annular heating assembly 315 utilizes a heated fluid. In certain embodiments, first annular heating assembly 315 generates infrared energy. In certain embodiments, first annular heating assembly 315 generates microwave energy.

Reactor 300 further comprises a plurality of injector nozzles 370 downstream from dissolution zone 310. The plurality of injector nozzles 370 are in communication with controller 400 via communication link 392.

Reactor 300 further comprises a second dissolution zone 320 downstream from, and adjacent to, injector nozzles 370, and a second annular heating assembly 325 disposed around second dissolution zone 320. The second annular heating assembly 325 is in communication with controller 400 via communication link 393. In certain embodiments, second annular heating assembly 325 comprises an electric heater. In certain embodiments, second annular heating assembly 325 utilizes a heated fluid. In certain embodiments, second annular heating assembly 325 generates infrared energy. In certain embodiments, second annular heating assembly 325 generates microwave energy.

Reactor 300 further comprises a plurality of injector nozzles 375 downstream from dissolution zone 320. The plurality of injector nozzles 375 are in communication with controller 400 via communication link 394.

Reactor 300 further comprises a third dissolution zone 330 downstream from, and adjacent to, injector nozzles 375, and a third annular heating assembly 335 disposed around third dissolution zone 330. The third annular heating assembly 335 is in communication with controller 400 via communication link 395. In certain embodiments, third annular heating assembly 335 comprises an electric heater. In certain embodiments, third annular heating assembly 335 utilizes a heated fluid. In certain embodiments, third annular heating assembly 335 generates infrared energy. In certain embodiments, third annular heating assembly 335 generates microwave energy.

Reactor 300 further comprises a plurality of injector nozzles 380 downstream from dissolution zone 330. The plurality of injector nozzles 380 are in communication with controller 400 via communication link 396.

Reactor 300 further comprises a fourth dissolution zone 340 downstream from, and adjacent to, injector nozzles 380, and a fourth annular heating assembly 345 disposed around fourth dissolution zone 340. The fourth annular heating assembly 345 is in communication with controller 400 via communication link 397. In certain embodiments, fourth annular heating assembly 345 comprises an electric heater. In certain embodiments, fourth annular heating assembly 345 utilizes a heated fluid. In certain embodiments, fourth annular heating assembly 345 generates infrared energy. In certain embodiments, fourth annular heating assembly 345 generates microwave energy.

Reactor 300 further comprises a plurality of injector nozzles 385 downstream from dissolution zone 340. The plurality of injector nozzles 385 are in communication with controller 400 via communication link 398.

Reactor 300 further comprises a fifth dissolution zone 350 downstream from, and adjacent to, injector nozzles 385, and a temperature adjustment assembly 355 disposed around fifth dissolution zone 350. The temperature adjustment assembly 355 is in communication with controller 400 via communication link 399. In certain embodiments, temperature adjustment assembly 355 comprises an electric heater. In certain embodiments, temperature adjustment assembly 355 utilizes a heated fluid. In certain embodiments, temperature adjustment assembly 355 generates infrared energy. In certain embodiments, temperature adjustment assembly 355 generates microwave energy.

In certain embodiments, temperature adjustment assembly 355 comprises a chiller. In certain embodiments, temperature adjustment assembly 355 utilizes a cooled fluid.

The product of continuous flow reactor 300 is expelled as product stream 360 from output end 307.

Figure 4:
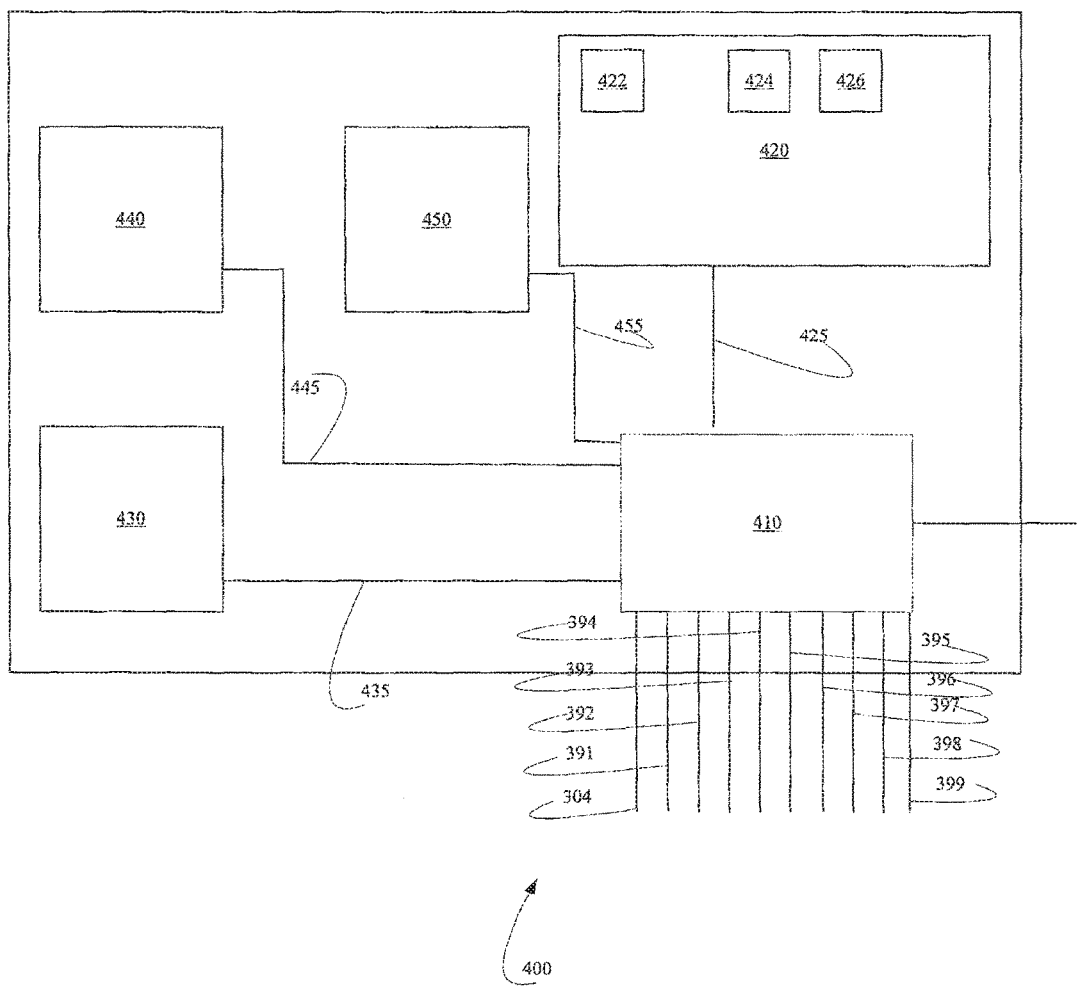
FIG. 4 illustrates one embodiment of Applicants' controller used to operate the continuous flow reactor of FIG. 3.

Referring now to FIG. 4, controller 400 comprises processor 410, memory 420 interconnected with processor 410 via communication link 425, optional Blue Tooth module 430 interconnected with processor 410 via communication link 435, optional RFID module 440 interconnected with processor 410 via communication link 445, and optional "WI-FI" module 450 interconnected with processor 410 via communication link 455.

In the illustrated embodiment of FIG. 4, microcode 422, computer readable program code 424, and database 426, are encoded in memory 420. In certain embodiments, memory 420 comprises non-volatile memory. In certain embodiments, memory 420 comprises battery backed up RAM, a magnetic hard disk assembly, an optical disk assembly, and/or electronic memory. By "electronic memory," Applicants mean a PROM, EPROM, EEPROM, SMARTMEDIA, FLASHMEDIA, and the like.

Processor 410 uses microcode 422 to operate controller 400. Processor 410 uses microcode 422, computer readable program code 424, and database 426, to operate Blue Tooth module 430, RFID module 440, WI-FI module 450, heating assemblies 315, 325, 335, 345, temperature adjustment assembly 355, injection pump 302, and injector nozzles 370, 377, 380, and 385.

FIG. 2 summarizes Applicants' method to prepare Applicants' catheter locking formulation. In step 210, Applicants' method supplies Trimethoprim, Propylene Glycol USP, Phosphate Buffered Saline Solution, EDTA Ca Disodium Hydrate, Glycerin USP, and Absolute Ethanol.

In step 220, the method dissolves trimethoprim in propylene glycol at a temperature greater than room temperature. In certain embodiments, the method in step 220 dissolves trimethoprim in propylene glycol and diethylene glycol. In certain embodiments, the method in step 220 dissolves trimethoprim in propylene glycol and ethylene glycol. In certain embodiments, the method in step 220 dissolves trimethoprim in propylene glycol, diethylene glycol, and ethylene glycol.

In certain embodiments, the temperature of step 220 is between about 50° C. and about 55° C. In certain embodiments, step 220 further comprises agitating/stirring the trimethoprim/propylene glycol mixture.

In certain embodiments, step 220 includes steps 1, 2, 3, and 4, of Process 2. In certain embodiments, step 220 includes steps 1, 2, and 3, of Process 3. In certain embodiments, step 220 includes steps 1, 2, and 3, of Process 4. In certain embodiments, step 220 includes injecting a trimethoprim/propylene glycol mixture into continuous flow reactor 300 via injector 302, wherein the temperature of heating assembly 315 and the rate of injection of the trimethoprim/propylene glycol mixture are set by controller 400 using processor 410, microcode 422, and computer readable program code 424.

In step 230, the method adds PBS buffer to the solution of step 220. In certain embodiments, step 230 is performed at a temperature greater than room temperature. In certain embodiments, step 230 is performed at the same temperature utilized in step 220. In certain embodiments, the temperature of step 230 is between about 50° C. and about 55° C. In certain embodiments, step 230 further comprises agitating/stirring the solution of step 220 and the added PBS buffer.

In certain embodiments, step 230 includes step 5 of Process 2. In certain embodiments, step 230 includes steps 4 and 5 of Process 3. In certain embodiments, step 230 includes step 4 of Process 4. In certain embodiments, step 230 includes injecting the PBS buffer solution into continuous flow reactor 300 via input injectors 370, wherein the temperature of heating assembly 325 and the rate of injection of the PBS buffer are set by controller 400 using processor 410, microcode 422, and computer readable program code 424.

In step 240, the method adds EDTA Ca Disodium Hydrate to the solution of step 230. In certain embodiments, step 240 is performed at a temperature greater than room temperature. In certain embodiments, step 240 is performed at the same temperature utilized in step 230. In certain embodiments, the temperature of step 240 is between about 50° C. and about 55° C. In certain embodiments, step 240 further comprises agitating/stirring the solution of step 230 and the added EDTA Ca Disodium Hydrate.

In certain embodiments, step 240 include step 6 of Process 2. In certain embodiments, step 230 includes step 6 of Process 3. In certain embodiments, step 240 includes step 5 of Process 4. In certain embodiments, step 240 includes injecting EDTA Ca Disodium Hydrate into continuous flow reactor 300 via input injectors 375, wherein the temperature of heating assembly 335 and the rate of injection of the EDTA Ca Disodium Hydrate are set by controller 400 using processor 410, microcode 422, and computer readable program code 424.

In step 250, the method adds Glycerin to the solution of step 240. In certain embodiments, the method in step 250 adds Glycerin and ethylene glycol to the solution of step 240. In certain embodiments, the method in step 250 adds Glycerin and diethylene glycol to the solution of step 240. In certain embodiments, the method in step 250 adds Glycerin, ethylene glycol, and diethylene glycol, to the solution of step 240.

In certain embodiments, step 250 is performed at a temperature greater than room temperature. In certain embodiments, step 250 is performed at the same temperature utilized in step 240. In certain embodiments, the temperature of step 250 is between about 50° C. and about 55° C. In certain embodiments, step 250 further comprises agitating/stirring the solution of step 240 and the added Glycerin.

In certain embodiments, step 250 include step 7 of Process 2. In certain embodiments, step 230 includes step 7 of Process 3. In certain embodiments, step 240 includes step 6 of Process 4. In certain embodiments, step 250 includes injecting Glycerin into continuous flow reactor 300 via input injectors injector 380, wherein the temperature of heating assembly 345 and the rate of injection of the Glycerin are set by controller 400 using processor 410, microcode 422, and computer readable program code 424.

In step 260, the method cools the solution of step 250 to room temperature. In certain embodiments, step 250 includes step 8 of Process 2. In certain embodiments, step 260 includes step 8 of Process 3. In certain embodiments, step 240 includes step 7 of Process 4. In certain embodiments, step 260 includes adjusting the temperature of the solution in portion 340 of continuous flow reactor 300, wherein the temperature of temperature adjustment assembly 355 is set by controller 400 using processor 410, microcode 422, and computer readable program code 424. In certain of the method using continuous flow reactor 300, step 260 is not performed.

In step 270, the method adds Absolute Ethanol to the solution of step 260. In certain embodiments, step 250 is performed at room temperature. In certain embodiments, step 270 further comprises agitating/stirring the solution of step 260 and the added Absolute Ethanol.

In certain embodiments, step 270 includes step 9 of Process 2. In certain embodiments, step 250 includes step 9 of Process 3. In certain embodiments, step 270 includes step 8 of Process 4. In certain embodiments, step 270 includes injecting Absolute Ethanol into continuous flow reactor 300 via input injectors 385, wherein the temperature of temperature adjustment assembly 355 and the rate of injection of the Absolute Ethanol are set by controller 400 using processor 410, microcode 422, and computer readable program code 424.

In certain embodiments, the composition of step 270 comprises the formulation of Table 3. In certain embodiments, the composition of step 270 comprises the formulation of Table 4. In certain embodiments, the composition of step 270 comprises the formulation of Table 5.

In certain embodiments, the composition of step 270 meets the nominal levels described hereinabove for Trimethoprim. In certain embodiments, the composition of step 270 meets the nominal levels described hereinabove for EDTA Ca Disodium Hydrate. In certain embodiments, the composition of step 270 meets the nominal levels described hereinabove for Absolute Ethanol.

In certain embodiments, the composition of step 270 meets the nominal value described hereinabove for density. In certain embodiments, the composition of step 270 meets the nominal value described hereinabove for viscosity. In certain embodiments, the composition of step 270 meets the nominal value described hereinabove for pH. In certain embodiments, the composition of step 270 meets the nominal value described hereinabove for impurities. In certain embodiments, the composition of step 270 meets the nominal value described hereinabove for osmolality. In certain embodiments, the composition of step 270 meets the nominal value described hereinabove for particulate matter.

In certain embodiments, Applicants' invention includes computer readable program code, such as and without limitation, computer readable program code residing memory 150 (FIG. 1), wherein those instructions are executed by a processor, such as processor 140 (FIG. 1), to perform one or more of steps 210-270 recited in FIG. 2.

In other embodiments, Applicants' invention includes instructions residing in any other computer program product, where those instructions are executed by a computer external to, or internal to, system 100, to perform one or more of steps 210-270 recited in FIG. 2. In either case, the instructions may be encoded in an information storage medium comprising, for example, a magnetic information storage medium, an optical information storage medium, an electronic information storage medium, and the like. By "electronic storage media," Applicants mean, for example, a device such as a PROM, EPROM, EEPROM, Flash PROM, compactflash, smartmedia, and the like.

While the preferred embodiments of the present invention have been illustrated in detail, it should be apparent that modifications and adaptations to those embodiments may occur to one skilled in the art without departing from the scope of the present invention as set forth in the following claims.

We claim:

1. A method to prepare a catheter locking formulation, comprising the following steps in the following order:
    dissolving trimethoprim in propylene glycol at a temperature between about 50° C. and about 55° C. with stirring for at least 60 minutes to form a solution of trimethoprim and propylene glycol;
    sequentially adding at a temperature between about 50° C. and about 55° C., in the following order, phosphate buffered saline, EDTA Calcium Disodium Hydrate, and glycerin, to said trimethoprim/propylene glycol solution, wherein glycerin should be added only after all solids have been completely solubilized;
    cooling said propylene glycol solution containing trimethoprim, propylene glycol, phosphate buffered saline, EDTA Calcium Disodium Hydrate, and glycerin to about room temperature;
    adding absolute ethanol at about room temperature to a room temperature solution of trimethoprim, propylene glycol, EDTA Calcium Disodium Hydrate, phosphate buffered saline, and glycerin to form a catheter locking solution;
    wherein said absolute alcohol is present at a level of at least fifteen (15) weight percent of said catheter locking solution;
    wherein said catheter locking solution maintains shelf life stability, including no formation of precipitates, at temperatures between 0° C. to about 42° C. for at least three days; and
    wherein said catheter locking solution comprises a pH between about 8 and about 9.

2. The method of claim 1, wherein said phosphate buffered saline comprises no calcium salts or magnesium salts.

3. The method of claim 1, wherein said adding phosphate buffered saline to the propylene glycol and trimethoprim solution comprises:
    adding sterile water to said propylene glycol and trimethoprim solution, at a temperature between about 50° C. and about 55° C.;
    mixing, at a temperature between about 50° C. and about 55° C., until a trimethoprim, propylene glycol, and water solution, is completely clear and uniform;
    adding NaCl, $KH_2PO_4$, and $Na_2HPO_4$ to said propylene glycol, trimethoprim, and water solution at a temperature between about 50° C. and about 55° C.

4. The method of claim 1, wherein the catheter lock solution has a nominal viscosity between about 4.0-6.0 cps at 25° C. and has a pH value between about 8 and about 9.

5. The method of claim 1, wherein the catheter lock solution has a nominal density set to match approximate human plasma density of about 1.02 g/ml.

6. A method to prepare a catheter locking solution, comprising the following steps in the following order:

dissolving trimethoprim in propylene glycol at a temperature between about 50° C. and about 55° C. to form a solution of trimethoprim and propylene glycol;

adding phosphate buffered saline to the solution of trimethoprim and propylene glycol at a temperature between about 50° C. and about 55° C. to form a solution of trimethoprim, propylene glycol, and phosphate buffered saline;

adding EDTA Calcium Disodium Hydrate to the solution of trimethoprim, propylene glycol, and phosphate buffered saline at a temperature between about 50° C. and about 55° C. to form a solution of trimethoprim, propylene glycol, phosphate buffered saline, and EDTA Calcium Disodium Hydrate;

adding glycerin to the solution of trimethoprim, propylene glycol, phosphate buffered saline, and EDTA Calcium Disodium Hydrate at a temperature between about 50° C. and about 55° C. to form a solution of trimethoprim, propylene glycol, phosphate buffered saline, EDTA Calcium Disodium Hydrate, and glycerin;

cooling the solution of trimethoprim, propylene glycol, phosphate buffered saline, EDTA Calcium Disodium Hydrate, and glycerin to about room temperature;

adding absolute ethanol at about room temperature to the solution of trimethoprim, propylene glycol, phosphate buffered saline, EDTA Calcium Disodium Hydrate, and glycerin, at about room temperature, to form said catheter locking solution;

wherein said phosphate buffered saline comprises an osmolality of about 287 milli-osmoles per kilogram; and wherein said catheter locking solution maintains shelf life stability, including no formation of precipitates, at temperatures between 0° C. to about 42° C. for at least three days.

7. The method of claim 6, wherein said phosphate buffered saline comprises no calcium salts or magnesium salts.

\* \* \* \* \*